United States Patent [19]

Böger

[11] Patent Number: 4,687,855

[45] Date of Patent: Aug. 18, 1987

[54] CERTAIN 3-TRIFLUOROMETHYL-5-CHLORO-2-PYRIDYLOXY-ANILINE INTERMEDIATES

[75] Inventor: Manfred Böger, Weil am Rhein, Fed. Rep. of Germany

[73] Assignee: Ciba-Geigy Corporation, Ardsley, N.Y.

[21] Appl. No.: 820,817

[22] Filed: Jan. 17, 1986

Related U.S. Application Data

[60] Continuation of Ser. No. 613,537, May 24, 1984, abandoned, which is a division of Ser. No. 439,457, Nov. 5, 1982, abandoned.

[30] Foreign Application Priority Data

Nov. 10, 1981 [CH] Switzerland .................. 7208/81
Oct. 8, 1982 [CH] Switzerland .................. 5925/82

[51] Int. Cl.$^4$ .................. C07D 213/61; C07D 213/64
[52] U.S. Cl. .................. 546/300; 546/291
[58] Field of Search .................. 546/300

[56] References Cited

U.S. PATENT DOCUMENTS 4,003,733  1/1977  Johnston .................. 71/94
4,173,637  11/1979  Nishiyama et al. .................. 514/351
4,310,530  1/1982  Nishiyama et al. .................. 514/351

FOREIGN PATENT DOCUMENTS 0025363  3/1981  European Pat. Off. .................. 514/346
0040179  11/1981  European Pat. Off. .................. 546/291
2058072  4/1981  United Kingdom .................. 514/346
1589259  5/1981  United Kingdom .................. 546/291

*Primary Examiner*—Alan L. Rotman

*Attorney, Agent, or Firm*—Edward McC. Roberts; Meredith C. Findlay

[57] ABSTRACT

Substituted N-3-(5-trifluoromethyl-pyridyl-2-oxy)phenyl-N'-benzoylureas of the formula

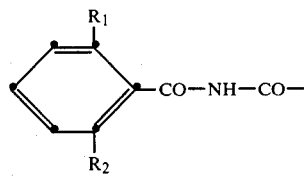

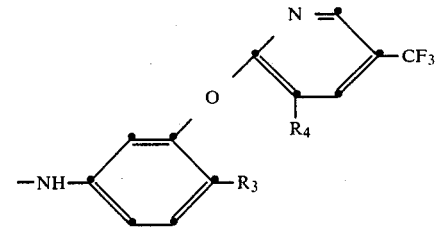

wherein $R_1$, $R_2$ and $R_3$ independently of one another are each hydrogen, methyl, fluorine, chlorine or bromine, and $R_4$ is hydrogen or chlorine, with the proviso that $R_3$ is methyl, fluorine, chlorine or bromine when $R_4$ is chlorine, are active substances having an insecticidal and, in particular, acaricidal action. They can be advantageously used to combat zooparasitic and phytoparasitic ectoparasites.

4 Claims, No Drawings

CERTAIN 3-TRIFLUOROMETHYL-5-CHLORO-2-PYRIDYLOXY-ANILINE INTERMEDIATES

This application is a continuation of application Ser. No. 613,537, filed May 24, 1984 abandoned, which is a division of application Ser. No. 439,457, filed Nov. 5, 1982, abandoned.

CROSS-REFERENCE TO RELATED APPLICATION

The present invention relates to novel substituted N-3-(5-trifluoromethyl-pyridyl-2-oxy)-phenyl-N'-benzoylureas, to processes for producing them, and to their use for combating pests. Novel starting materials and the production thereof also form subject matter of the invention.

The substituted N-3-(5-trifluoromethyl-pyridyl-2-oxy)-phenyl-N'-benzoylureas according to the invention have the formula I

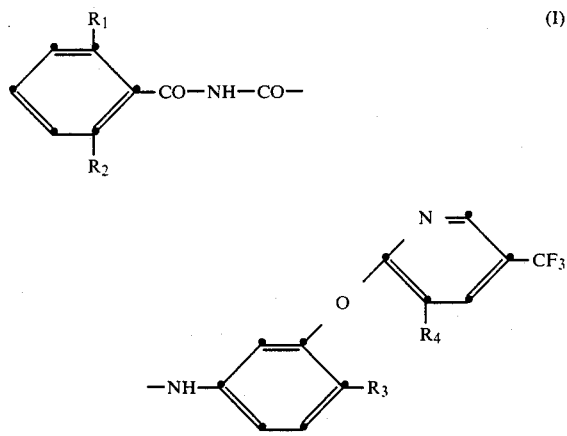

wherein
R$_1$, R$_2$ and R$_3$ independently of one another are each hydrogen, methyl, fluorine, chlorine or bromine, and
R$_4$ is hydrogen or chlorine, with the proviso that R$_3$ is methyl, fluorine, chlorine or bromine when R$_4$ is chlorine.

Preferred compounds of the formula I on account of their action as pesticidal active substances are those wherein R$_1$ is methyl, fluorine or chlorine, R$_2$ is hydrogen, methyl, fluorine or chlorine, R$_3$ is hydrogen, methyl, fluorine, chlorine or bromine, and R$_4$ is hydrogen or chlorine. Of particular interest are also those compounds of the formula I wherein R$_1$ is fluorine or chlorine, R$_2$ is hydrogen or fluorine, R$_3$ is hydrogen, methyl or chlorine, and R$_4$ is hydrogen or chlorine.

More especially preferred are compounds of the formula I wherein R$_3$ and/or R$_4$ are (or is) hydrogen. To be emphasised are in particular those compounds of the formula I wherein R$_1$ and R$_2$ are fluorine.

The compounds of the formula I can be produced by processes analogous to known processes (cp. inter alia, the German Offenlegungsschriften Nos. 2,123,236 and 2,601,780).

A compound of the formula I can thus be obtained for example by reaction
(a) of a compound of the formula II

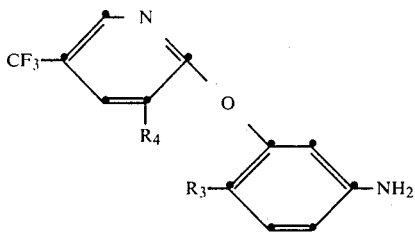

with a compound of the formula III

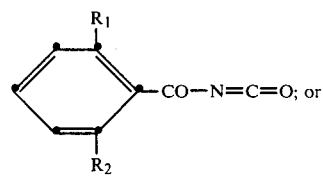

(b) of a compound of the formula IV

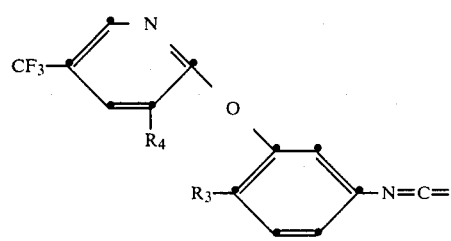

optionally in the presence of an organic or inorganic base, with a compound of the formula V

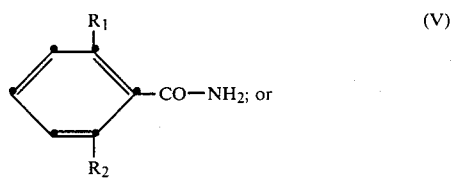

(c) of a compound of the formula II with a compound of the formula VI

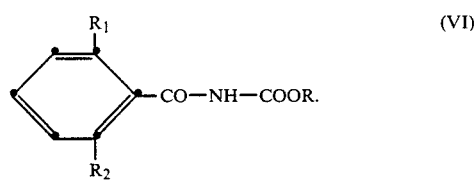

In the above formulae II to VI, the symbols R$_1$ to R$_4$ have the meanings defined under the formula I given in the foregoing, and R is a C$_1$-C$_8$-alkyl group, which is unsubstituted or substituted by halogen.

The stated processes (a), (b) and (c) are preferably performed under normal pressure and in the presence of an organic solvent or diluent. Suitable solvents or diluents are for example: ethers and etheral compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; nitriles, such as acetonitrile or propionitrile; dimethyl sulfoxide, as well as ketones, for example acetone, methyl ethyl ketone, methylisopropyl ketone and methylisobutyl ketone. Process (a) is generally performed at a temperature of −10° to 100° C., preferably between 15° and 25° C., optionally in the presence of an organic base, for example triethylamine. Process (b) is performed at a temperature of 0° to 150° C., preferably at the boiling point of the employed solvent, and optionally in the presence of an organic base, such as pyridine, and/or with the addition of an alkali metal or alkaline-earth metal, preferably sodium. For the process (c), that is, for the reaction of the urethane of the formula VI with the aniline of the formula II, preferred temperatures are between about 60° C. and the boiling point of the reaction mixture concerned, the solvents used being in particular aromatic hydrocarbons, such as toluene, xylene, chlorobenzene, and the like.

The starting materials of the formulae III, V and VI are known and can be produced by processes analogous to known processes. In the case of the starting materials of the formulae II and IV, they are in part novel compounds which can be produced by procedures known per se (cp. for example the U.S. Pat. Nos. 3,705,170 and 3,711,486).

5-Trifluoromethylpyridyl-2-oxy-anilines of the formula II can be produced as follows:

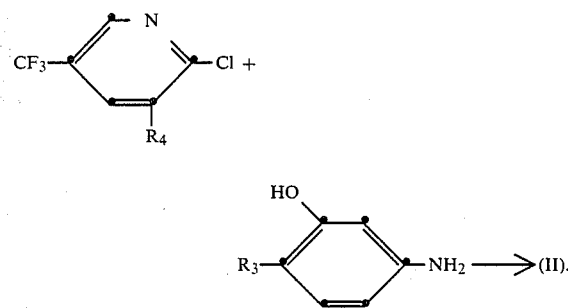

This reaction is performed at a temperature of 20°–180° C., preferably at 50°–160° C., in the presence of an acid acceptor, for example of a hydroxide or hydride of an alkali metal or alkaline-earth metal, preferably KOH or NaOH, as well as of an inert organic solvent, preferably dimethyl formamide or dimethyl sulfoxide. Furthermore, an aniline of the formula II can be produced by hydrogenation of the corresponding nitro compounds, using a process analogous to that described in J. Org. Chem. 29 (1964), 1 (cp. also the literature cited therein); anilines of the formula II are obtainable also by chemical reduction (for example by means of Sn-(II)-chloride/HCl) of a corresponding nitro compound (cp. Houben Weyl, "Methoden d. org. Chemie" 11-/1, 422):

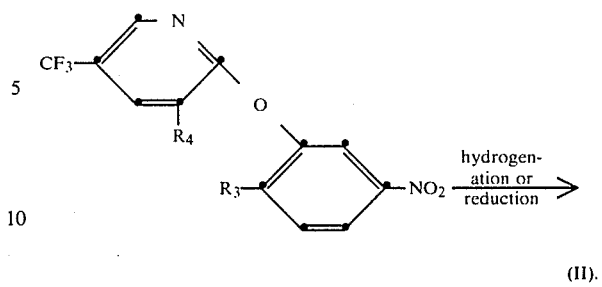

The present invention relates also to the novel compounds of the formula II wherein $R_4$ is hydrogen, and $R_3$ is hydrogen, methyl, fluorine, chlorine or bromine, or wherein $R_4$ is chlorine, and $R_3$ is methyl, fluorine, chlorine or bromine. Benzoylisocyanates of the formula III can be obtained, inter alia, as follows (cp. J. Agr. Food Chem. 21, 348 and 993; 1973):

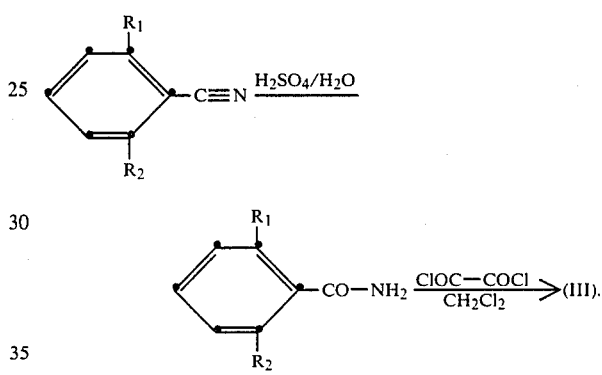

A 3-(5-trifluoromethylpyridyl-2-oxy)-phenylisocyanate of the formula IV can be produced, using in general customary processes, e.g. by reacting an aniline of the formula II with phosgene. The benzamides of the formula V also to be used as starting materials are known [cp., for example, Beilstein "Handbuch der organischen Chemie" (Handbook of organic Chemistry), Vol. 9, p. 336].

Urethanes of the formula VI can be obtained, in a manner known per se, by reaction of a benzoylisocyanate of the formula III with a corresponding alcohol, or by reaction of a benzamide of the formula V, in the presence of a basic compound, with a corresponding ester of chloroformic acid.

It is already known that specific substituted N-phenoxyphenyl-N′-benzoylureas have insecticidal properties. From the German Offenlegungsschriften Nos. 2,504,982 and 2,537,413 are thus known halogen-substituted N-4-(2-chloro4-trifluoromethyl-phenoxy)-phenyl-N′-benzoylureas which have insecticidal activity. The Japanese Patent Specification No. 5-301447 relates to N-4-(trifluoromethylphenoxy)-phenyl-N′-benzoylureas as insecticidal active substances. In the German Offenlegungsschriften Nos. 2,748,636 and 2,818,830, in the European Patent Application No. 0025363, as well as in the Japanese Patent Application No. 54-115380, there is described, inter alia: N-4-(5-trifluoromethyl-pyridyl-2-oxy)-phenyl-N′-benzoylureas having selective insecticidal activity, that is to say, useful insects are not affected, whereas harmful insects are combated.

Compared with the compounds cited above, the compounds of the formula I according to the present invention are novel substituted N-3-(5-trifluoromethyl-pyridyl-2-oxy)-phenyl-N'-benzoylureas which surprisingly have a greater insecticidal activity, especially against harmful eating insects, such as *Spodoptera littoralis* and *Heliothis virescens*. A further advantage of the compounds of the formula I according to the invention is that they have negligible toxicity to warm-blooded animals, whilst having high tolerance to plants.

The compounds of the formula I are particularly suitable for combating insects of the orders: Lepidoptera, Coleoptera, Homoptera, Heteroptera, Diptera, Thysanoptera, Othoptera, Anoplura, Siphonaptera, Mallophaga, Thysanura, Isoptera, Psocoptera and Hymenoptera.

Besides having a very favourable action against flies, for example *Musca domestica*, and against mosquito larvae, the compounds of the formula I can be used also for combating insects that damage plants by eating, in crops of ornamental plants and productive plants, especially in cotton crops (for example against *Spodoptera littoralis* and *Heliothis virescens*), and also in fruit and vegetable crops (for example against *Laspeyresia pomonella*, *Leptinotarsa decemlineata* and *Epilachna varivestis*). The compounds of the formula I are characterised by a marked action against larval insect stages, especially against larval stages of harmful eating insects. When compounds of the formula I are taken up with the feed by adult insects, there is observed in many cases, particularly with Coleoptera, for example *Anthonomus grandis*, a reduced oviposition and/or a lessened rate of hatching.

The compounds of the formula I are suitable also for combating ectoparasites, such as *Lucilia sericata*, in both domestic and productive animals, for example by treatment of animals, livestock housing and pasture land.

The N-phenoxyphenyl-N'-benzoylureas hitherto known are described in the literature as being almost exclusively insecticidally effective. Only passing observations have been made concerning other effects. An apparent acaricidal action is mentioned briefly for example in the German Offenlegungsschrift No. 2,504,982, but no proof of it is provided.

The fact now is particularly surprising, and it could not have been expected in the light of the prior known literature, that the compounds of the formula I of the present invention not only have a favourable insecticidal action, but also an especially pronounced acaricidal action which applies, in particular, to zooparasitic members of the order Acarina. The acaricidal use of the compounds of the formula I forms additional subject matter of the present invention. The special advantage is the possibility of combating all the Acarina development stages, so that a single application destroys both adult pests as well as nymphs, larvae and eggs. It was possible to verify on cattle artificially infested with *Boophilus microplus* larvae that 2½ to 3 weeks after application neither adult ticks nor their development stages were to be found on the animals, and that no new infestation had occurred during the following period. This finding is extraordinarily surprising, and it moreover provides evidence of an additional and quite unexpected novel prolonged action of the preparations of the formula I.

By virtue of this marked double action against insects and against pests of the order Acarina, compounds of the formula I according to the present invention are excellently suitable for combating ectoparasites of all kinds, that is to say, both phytoparasitic and, in particular, zooparasitic members.

The last-mentioned group includes both parasitic flies (and their development stages) of the genera: Musca, Fannia, Haematobia, Stomoxis, Glossina, Hippobosca, Lucilia, Calliphora, Phormia, Sarcophaga, Wohlfahrtia, Cochliomyia, Chrysomyia, Cordylobia, Dermatobia, Cuterebra, Gastrophilus, Oestrus, Hypoderma, and others; as well as ticks and mites of the genera: Ixodes, Ripicephalus, Amblyomma, Hyalomma, Haemaphysalis, Boophilus, Ornithodorus, Argas, Dermanyssus, Ornithonyssus, Psoroptes, Chorioptes, Sarcoptes, and the like.

The active substances are applied according to the invention in the veterinary field, in a known manner, by oral application in the form for example of: tablets, capsules, lick-stones, bolusses, drinking water or granulates, or by dermal application in the form for example of: dipping, spraying, pour-on or spot-on and powdering, or by parenteral administration by means of injection or an implant, or by transdermal application with capsules attached to the skin.

The action of the compounds according to the present invention or of the compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, carbamates, chlorinated hydrocarbons and *Bacillus thuringiensis* preparations.

The compounds of the formula I can be combined with particular advantage also with substances intensifying pesticidal activity. Examples of such compounds are, inter alia: piperonylbutoxide, propynyl ethers, propynyl oximes, propynyl carbamates and propynyl phosphonates, 2-(3,4-methylenedioxyphenoxy)-2,6,9-trioxaundecane or S,S,S-tributylphosphorotrithioates.

The compounds of the formula I are used either in an unmodified form, or preferably together with auxiliaries customarily employed in formulation practice, and are thus processed, in a known manner, for example into the form of emulsion concentrates, directly sprayable, dilutable or parenterally injectable solutions, diluted emulsions, wettable powders, soluble powders, dusts, granulates or compressed preparations, and also encapsulations in for example polymeric substances. The application processes, such as spraying, atomising, dusting, scattering, pouring, oral application or injection, and likewise the type of preparations, are selected to suit the objectives to be achieved and the given conditions.

The formulations, that is to say, the compositions or preparations containing the active ingredient of the formula I, or combinations of this active ingredient with other insecticides or acaricides, and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalates, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acids or highly dispersed absorbent polymers. Suitable granulated adsorptive carriers are porous types, for example pumice, ground brick, sepiolite or bentonite; and suitable nonsorbent carriers are materials such as calcite or sand. A great number of pre-granulated materials of inorganic or organic nature, such as in particular dolomite or ground plant residues, can also be used.

Suitable auxiliaries for the compressed preparations are the customary binders, such as dextrine, cellulose derivatives, sorbitol and polyvinylpyrrolidone; fillers, such as cellulose, lactose and various types of starch; lubricants, such as alkaline-earth metal salts of higher fatty acids, for example calcium stearate; and auxiliaries accelerating decomposition, such as alginates and avicel, and also starch derivatives.

Suitable surface-active compounds are, depending on the nature of the active ingredient of the formula I, or of the combinations of this active ingredient with other insecticides or acaricides, to be formulated, nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$-$C_{22}$), for example the sodium or potassium salts of oleic or stearic acid, or of natural fatty acid mixtures, which can be obtained for example for coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having about 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylehesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi-(2-chloroethyl)-ethyl-ammonium bromide.

The tensides customarily used in formulation practice are described, inter alia, in the following publications:

"Mc Cutcheon's Detergents and Emulsifiers Annual", MC Publishing Corp., Ringwood, N.J., 1979, and Sisely and Wood, "Encyclopedia of Surface Active Agents", Chemical Publishing Co., Inc. New York (1979).

The pesticidal preparations contain as a rule 0.1 to 99%, particularly 0.1 to 95%, of active ingredient of the formula I, or of combinations of this active ingredient with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule diluted preparations having considerably lower concentrations of active ingredient.

The compositions can also contain additives, such as stabilisers, antifoaming agents, viscosity regulators, binders and adhesives, as well as ferilisers or other active substances for obtaining special effects.

Formulation Examples for solid active ingredients of the formula I or combinations of these active ingredients with other insecticides or acaricides
(%=percent by weight)

| 1. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalenesulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active-ingredient combination is well mixed with the additives, and the mixture is thoroughly ground in a suitable mill. Wettable powders which can be diluted with water to give suspensions of the required concentration are obtained. These powders can be administered with the feed.

| 2. Emulsion concentrate | |
|---|---|
| active ingredient or active-ingredient combination | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 3. Dusts | (a) | (b) |
|---|---|---|
| active ingredient or active-ingredient combination | 5% | 8% |
| talcum | 95% | — |
| kaolin | — | 92% |

Dusts ready for use are obtained by mixing the active ingredient with the carrier, and grinding the mixture in a suitable mill. Dusts can be applied directly or added to the feed.

| 4. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded, granulated and subsequently dried in a stream of air. Granulates of this type are suitable as feed additives.

| 5. Coated granules | |
|---|---|
| active ingredient or active-ingredient combination | 3% |
| polyethylene glycol (MG 200) | 3% |
| kaolin | 94% |

The finely ground active ingredient or the active-ingredient combination is evenly applied, in a mixer, to the kaolin moistened with polyethylene glycol. Dust-free coated granules are obtained in this manner. Granules of this type are suitable as feed additives.

| 6. Suspension concentrate | |
|---|---|
| active ingredient or active-ingredient combination | 40% |
| ethylene glycol | 10% |
| nonylphenol-polyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |

| 6. Suspension concentrate -continued | |
|---|---|
| water | 32% |

The finely ground active ingredient or the active-ingredient combination is intimately mixed with the additives. The result is a suspension concentrate from which can be prepared, by dilution with water, suspensions of the concentration required. Suspension concentrates can also be administered to the animal orally (drench).

| 7. Compressed preparations | | |
|---|---|---|
| I | active ingredient or active-ingredient combination | 33.0% |
| | methylcellulose | 0.8% |
| | silicic acid (highly dispersed) | 0.8% |
| | maize starch | 8.4% |
| II | lactose (crystalline) | 22.5% |
| | maize starch | 17.0% |
| | microcrystalline cellulose | 16.5% |
| | magnesium stearate | 1.0% |

The auxiliaries of phase I are granulated together with the active ingredient or active-ingredient combination with the addition of 16.5 parts of water, and the whole is then mixed with the auxiliaries of phase II. The mixture is pressed into the form of tablets or boluses, and subsequently dried.

Production Example 2.7 g of 2,6-difluorobenzoylisocyanate in 20 ml of water-free toluene are added to 4.5 g of (3-(3-chloro-5-trifluoromethyl-pyridyl-2-oxy)-4-methylaniline in 50 ml of water-free toluene. After the initially exothermic reaction has subsided, the mixture is left to stand overnight. After filtration and washing, there is obtained, in the form of white crystals, N-3-(3-chloro-5-trifluoromethyl-pyridyl-2-oxy)-4-methylphenyl-N'-2,6-difluorobenzoylurea, m.p. 178°–179° C. (compound No. 1).

Preparation of the starting compound 6.4 g of potassium hydroxide are placed into 30 ml of dimethyl sulfoxide, and to this mixture is added dropwise a solution of 15.3 g of 2-methyl-5-nitrophenol dissolved in 30 ml of dimethyl sulfoxide. After the exothermic reaction has subsided, there are slowly added dropwise 19.9 g of a mixture of 2-fluoro-3-chloro-5-trifluoromethylpyridine (40% by weight) and 2,3-dichloro-5-trifluoromethylpyridine (60% by weight). After this exothermic reaction too has subsided, the reaction mixture is stirred for a further ten hours; it is then poured into ice-water and extracted with dichloromethane. The extract is dried, and concentrated by evaporation. The residue is chromatographed with a mixture of dichloromethane and hexane (volume ratio 35:15) through silica gel, pure dichloromethane being used as the eluant at the start and at the end of the chromatographic process. The filtrate obtained is concentrated by evaporation, and recrystallised from hexane to thus obtain 3-(3-chloro-5-trifluoromethylpyridyl-2-oxy)-4-methyl-nitrobenzene as a white crystalline powder, m.p. 93°–94° C. This resulting compound is then hydrogenated in dioxane with Raney nickel as catalyst. The catalyst is filtered off; the reaction solution collected as filtrate is subsequently dissolved in dichloromethane, and chromatographed through silica gel to obtain 3-(3-chloro-5-trifluoromethyl-pyridyl-2-oxy)-4-methylaniline as white crystalline powder, m.p. 55° C., (Cpd. A).

The following compounds of the formula I are produced by methods analogous to those described in the foregoing, or by one of the reactions given earlier in the text:

TABLE I

| Compound No. | $R_1$ | $R_2$ | $R_3$ | $R_4$ | Melting point [°C.] |
|---|---|---|---|---|---|
| 1 | F | F | $CH_3$ | Cl | 178–179 |
| 2 | F | F | H | H | 186–188 |
| 3 | Cl | H | H | H | 136–138 |
| 4 | F | F | Br | Cl | 198–200 |
| 5 | Cl | Cl | Br | Cl | 216–218 |
| 6 | Cl | H | Br | Cl | 213–214 |
| 7 | Cl | H | $CH_3$ | Cl | 162–164 |
| 8 | H | H | $CH_3$ | Cl | 228–229 |
| 9 | F | F | Br | H | 190–194 |
| 10 | $CH_3$ | H | $CH_3$ | H | 140–145 |
| 11 | Br | H | $CH_3$ | Cl | 164–165 |
| 12 | $CH_3$ | H | $CH_3$ | Cl | 177–178 |
| 13 | Cl | H | $CH_3$ | H | 143–144 |
| 14 | Br | Br | $CH_3$ | Cl | 219–222 |
| 15 | F | F | $CH_3$ | H | 188–189 |
| 16 | F | F | F | Cl | 174–177 |
| 17 | F | F | Cl | Cl | 185–189 |
| 18 | F | F | F | H | 183–184 |
| 19 | F | F | Cl | H | 185–188 |

The compounds Nos. 4, 16, 17, 18 and 19 are particularly preferred as ectoparasiticidal active substances for combating parasitic insects (*Lucilia sericata, L. cuprina,* and so forth) and acarides.

Further subject matter of the present invention are ectoparasiticidal compositions containing as active ingredient a compound of the formula I, especially one of the compounds No. 4, 16, 17, 18 or 19.

The invention relates also to processes for combating parasitic insects and Acarina by means of compounds of the formula I, particularly by means of any one of the compounds Nos. 4, 16, 17, 18 and 19.

TABLE II

| (Compounds of formula II) | | | | | | | |
|---|---|---|---|---|---|---|---|
| Compound | $R_3$ | $R_4$ | m.p. | Compound | $R_3$ | $R_4$ | m.p. |
| A | $CH_3$ | Cl | 55° | E | Cl | Cl | 82–85° |
| B | H | H | 53–55° | F | F | Cl | 49–52° |
| C | Br | Cl | 79–81° | G | F | H | 54–57° |
| D | $CH_3$ | H | 64–66° | H | Cl | H | 63–65° |

Biological Examples

Example 1: Action against *Musca domestica*

50 g of freshly prepared CSMA nutrient medium for maggots are weighed off into each of a series of beakers. A specific amount of a 1% (by weight) acetonic solution of the respective active ingredient is transferred by pipette to the nutrient medium in each beaker. After a thorough mixing of the nutrient medium, the acetone is allowed to evaporate off for at least 20 hours. There are then deposited per active ingredient and concentration in each case 25 one-day-old *Musca domestica* maggots into each beaker containing the treated nutrient medium. After completion of pupation, the formed pupae are separated from the nutrient medium by flushing with water, and placed into vessels closed with perforated lids. The pupae flushed out per batch are counted (toxic effect of the active ingredient on the development of the maggots), and after 10 days the number of flies which have emerged from the pupae is determined.

Compounds of the formula I exhibited in the above test a complete destructive action (mortality 100%).

Example 2: Action against *Aëdes aegypti*

Sufficient of a 0.1% acetonic solution of the respective active ingredient is transferred by pipette to the surface of 150 ml of water in a container to obtain concentrations of 800 and 400 ppm, respectively. After the acetone has been evaporated off, 30–40 two-day-old Aëdes larvae are placed into the container. The mortality rate is ascertained after 1, 2 and 5 days.

The compounds Nos. 1 to 19 of the formula I resulted in a 100% mortality rate after just one day.

Example 3: Insecticidal stomach-poison action

Potted cotton plants about 25 cm in height are sprayed with aqueous active-ingredient emulsions containing the active ingredient in concentrations of 12.5 and 100 ppm, respectively. After drying of the applied coating, larvae of *Spodoptera littoralis* and of *Heliothis virescens*, all in the third larval stage, are settled onto the cotton plants. The test is carried out at 24° C. with 60% relative humidity. An assessment is made after 120 hours of the % mortality of the test insects compared with that in the case of untreated control specimens.

The following Table shows results of biological tests of compounds according to the invention on the basis of the above biological Example. The assessment of the test is made according to the resulting % mortality rate using the evaluation index given below:

A: 80–100% mortality at a concentration of the tested compound of 12.5 ppm,
B: 80–100% mortality at a concentration of the tested compound of 100 ppm.

| Compound No. | Pesticidal effectiveness | |
|---|---|---|
| | Spodoptera larvae | Heliothis larvae |
| 1 | A | A |
| 2 | A | A |
| 3 | A | A |
| 4 | A | B |
| 7 | B | A |

In active-ingredient concentrations of 400 ppm, the compounds Nos. 1–19 effect after 2 days a 100% destruction of L-4 larvae of the Mexican bean beetle.

Example 4

Reproduction-inhibiting effect on ticks

Fresh females of the tick species *Boophilus microplus*, which have sucked themselves full, are stuck in dorsal position, in rows each of 10 ticks, onto PVC sheets, and covered with a cotton-wool pad. Over each row are then poured 10 ml of the aqueous test solution. The cotton-wool pad is removed one hour later, and the ticks are dried overnight at 24° C. After drying, the ticks are kept at 28° C. with 80% relative humidity for 4 weeks until the end of oviposition and commencement of hatching of the larvae.

Each test substance is tested at 5 concentrations from 1000 to 64 ppm (dilution factor 2). The acaricidal action is manifested either in respect of mortality or sterility of the female, or in respect of oviposition by a blocking of the embryogenesis or of the act of hatching. All substances are tested against two different tick strains, the normally sensitive strain YEERONGPILLY and the OP-resistant strain BIARRA.

The activity of a substance is assessed on the basis of the lowest, still approximately fully-effective concentration (I R 100~100% inhibition of reproduction).

The compounds Nos. 1 to 19 of the formula I exhibited in this test a clear, reproduction-inhibiting action at concentrations between 64 and 500 ppm. The compounds Nos. 1, 4, 13 and 16 to 19 are completely effective at 64 ppm.

Example 5

Action against blowflies

Freshly deposited eggs of the blowfly species *Lucilia sericata* and *L. cuprina* are placed in small portions (30–50 eggs) into test tubes, in which previously 4 ml of nutrient medium has been mixed with 1 ml of test solution in the intermediate dilution of the active substance necessary for the final concentration. After inoculation of the culture medium, the test tubes are closed with a cotton-wool plug, and incubated in an incubator at 30° C. for 4 days. There develop by this time in the untreated medium about 1 cm long larvae (stage 3). Where a substance is active, however, the larvae at this point of time are either dead or moribund and clearly retarded. The test is carried out with 5 concentrations simultaneously of 100, 40, 16, 6.4 and 2.56 ppm. The criterion taken as a measure of effectiveness is the lowest concentration which is still fully effective (LC 100).

The good larvicidal action of compounds Nos. 1 to 19 of the formula I was verified in this test by the 100% mortality of the larvae occurring at the latest up to 96 hours at concentrations of between 40 and 2.56 ppm.

The compounds Nos. 2, 3, 4, 7, 13 and 15 to 19 where fully effective at a concentration of 6.4 ppm.

What is claimed is:

1. A compound of the formula

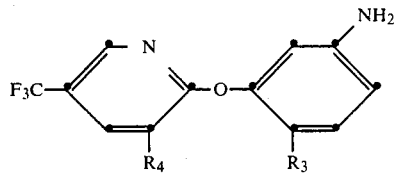

wherein $R_3$ is methyl, chlorine or bromine; $R_4$ is chlorine.

2. A compound of claim 1, wherein $R_3$ is chlorine and $R_4$ is chlorine.

3. The compound of claim 1, wherein $R_3$ is methyl and $R_4$ is chlorine.

4. The compound of claim 1, wherein $R_3$ is bromine and $R_4$ is chlorine.

* * * * *